(12) United States Patent
Fujiwara et al.

(10) Patent No.: US 9,339,055 B2
(45) Date of Patent: May 17, 2016

(54) T CELL APOPTOSIS INDUCER AND METHOD THEREFORE

(75) Inventors: Shigeru Fujiwara, Kanagawa (JP);
Hiroki Kanzato, Kanagawa (JP);
Satoshi Hachimura, Tokyo (JP)

(73) Assignee: ASAHI GROUP HOLDINGS, LTD., Tokyo (JP)

( * ) Notice: Subject to any disclaimer, the term of this patent is extended or adjusted under 35 U.S.C. 154(b) by 1186 days.

(21) Appl. No.: 13/167,483

(22) Filed: Jun. 23, 2011

(65) Prior Publication Data

US 2011/0250189 A1 Oct. 13, 2011

Related U.S. Application Data

(63) Continuation of application No. 11/883,377, filed as application No. PCT/JP2006/304243 on Mar. 6, 2006, now abandoned.

(30) Foreign Application Priority Data

Mar. 4, 2005 (JP) .................................. 2005-060285
Mar. 24, 2005 (JP) .................................. 2005-086546

(51) Int. Cl.
| | | |
|---|---|---|
| C12N 1/20 | (2006.01) | |
| A23L 1/30 | (2006.01) | |
| A61K 35/745 | (2015.01) | |
| A61K 35/747 | (2015.01) | |
| C12R 1/225 | (2006.01) | |
| C12R 1/23 | (2006.01) | |

(52) U.S. Cl.
CPC ............. *A23L 1/3014* (2013.01); *A61K 35/745* (2013.01); *A61K 35/747* (2013.01); *C12N 1/20* (2013.01); *C12R 1/225* (2013.01); *C12R 1/23* (2013.01); *A23Y 2220/05* (2013.01); *A23Y 2300/55* (2013.01)

(58) Field of Classification Search
CPC ............ A61K 2300/00; A61K 35/747; A61K 35/745; A61K 35/744; A61K 31/198; A61K 31/20; A61K 31/555; A61K 31/695; A61K 31/7008; A61K 31/737; A61K 38/47; A61K 2035/115; A61K 35/74; A61K 35/741; A61K 45/06; A23L 1/3014; A23Y 2220/05; A23Y 2300/55; C12N 1/20; C12R 1/225; C12R 1/23
See application file for complete search history.

(56) References Cited

U.S. PATENT DOCUMENTS

| | | | |
|---|---|---|---|
| 5,707,854 | A | 1/1998 | Saito et al. |
| 2003/0215429 | A1 | 11/2003 | De Simone |
| 2004/0009490 | A1 | 1/2004 | Glenn et al. |
| 2004/0115179 | A1 | 6/2004 | Liu et al. |
| 2004/0208863 | A1 | 10/2004 | Versalovic et al. |
| 2005/0214270 | A1 | 9/2005 | Yamamoto et al. |
| 2008/0166787 | A1 | 7/2008 | Fujiwara et al. |
| 2010/0040735 | A1 | 2/2010 | Fujiwara et al. |

FOREIGN PATENT DOCUMENTS

| | | |
|---|---|---|
| EP | 1 555 028 A1 | 7/2005 |
| EP | 1854468 A1 | 11/2007 |
| JP | 7-265064 A | 10/1995 |
| JP | 10-229841 A | 9/1998 |
| JP | 10-309178 A | 11/1998 |
| JP | 2002-504324 A | 2/2002 |
| JP | 2002-306125 A | 10/2002 |
| JP | 2004-26729 A | 1/2004 |
| JP | 2004-277381 A | 10/2004 |
| WO | WO 99/42568 A1 | 8/1999 |
| WO | WO 03/010297 A1 | 2/2003 |
| WO | WO 03045405 A2 | 6/2003 |
| WO | WO 2004/076615 A2 | 9/2004 |
| WO | WO 2006/073145 A1 | 7/2006 |
| WO | WO 2006/093313 A1 | 9/2006 |

OTHER PUBLICATIONS

Extended European Search Report, dated Mar. 20, 2013, for European Application No. 13154417.3.
Takeshi et al., "Antiallergic Agent and Fermented Food Containing Bifidus bacterium as Active Component", Database EPODOC European Patent Office, The Hague, NL, JP-13448297-A, Wakamoto Pharma Co. Ltd., XP-002693039, Nov. 24, 1998, 2 pages.
Fedorak et al., "Probiotics and the Management of Inflammatory Bowel Disease", InFlamm. Bowel Dis., vol. 10, No. 3, May 20, 2004, pp. 286-299.
Taiwanese Office Action dated Aug. 5, 2011, for Taiwanese Application No. 095107321.
Akdis M. et al., The FASEB Journal, vol. 17, 2003, pp. 1026-1035.
Boirivant et al., Gastroenterology, Mar. 1999, vol. 116, No. 3, p. 557 (Abstract only).
Guerra et al., J. Allergy Clin. Immunol. Apr. 2001, vol. 107, No. 4, pp. 647-653.
Ina K. et al., The Journal of Immunology, vol. 163, 1999, pp. 1081-1090.
International Preliminary Report on Patentability, Appl. No. PCT/JP2006/304243, May 30, 2007.
International Search Report dated Jun. 13, 2006 in International Application No. PCT/JP2006/304243.
Ishida et al., Journal of Dairy Science, vol. 88, No. 2, 2005, 2, pp. 527-533.
Watanabe-Fukunaga et al., Nature, Mar. 1992, vol. 356, pp. 314-317.
Y. Ishida et al., Biosci. Biotechnol. Biochem., 67(5), pp. 951-957, 2003.

(Continued)

*Primary Examiner* — Debbie K Ware
(74) *Attorney, Agent, or Firm* — Birch, Stewart, Kolasch & Birch, LLP

(57) ABSTRACT

An inducer of T cell apoptosis and a health food for inducing T cell apoptosis comprising as an active ingredient of a lactic acid bacterium belonging to the genus *Lactobacillus* or the genus *Bifidobacterium* are disclosed. Particularly preferred lactic acid bacteria belonging to the genus *Lactobacillus* or the genus *Bifidobacterium* are *Lactobacillus acidophilus* L-92 (FERM BP-4981), *Lactobacillus amylovorus* CP1750 (FERM BP-10532), *Bifidobacterium catenulatum* CP2829 (FERM BP-10533) and *Bifidobacterium longum* CP760 (FERM BP-10531). The inducer of T cell apoptosis of the invention is useful in the prevention and cure of a disease such as an organ-specific autoimmune disease or type I allergy.

12 Claims, 3 Drawing Sheets

(56) References Cited

OTHER PUBLICATIONS

Y. Ishida, Japan Food Science, vol. 43, No. 2, 2004, pp. 29-33 (English translation).

Yu Ishida, Japan Food Science, vol. 43, No. 2, 2004 pp. 29-33.

Carol et al., "Certain Strains of Lactobacillus can overcome resistance to apoptosis in T lymphocytes from patients with Crohn's disease," Inflammatory Bowel Diseases, vol. 9, No. 7, Supplement 1, Mar. 2003, p. S34.

Chinese Office Action, dated May 18, 2011, for Chinese Application No. 200780051609.X, including English translation.

Extended European Search Report, dated Dec. 30, 2010, for European Application No. 07850807.4.

Geng, "New Probiotics—Effects of Lactoamilovorin upon Piglets," Scientific Information of Animal Husbandry Veterinary Medicine, vol. 4, Dec. 31, 2001.

Gorbach, "Probiotics and Gastrointestinal Health," American Journal of Gastroenterology, vol. 95, No. 1, 2000, Suppl. 1, pp. S2-S4.

International Search Report, dated Jan. 29, 2008, for International Application No. PCT/JP2007/074321.

Japanese Office Action, dated Dec. 20, 2011, for Japanese Application No. 2007-506047, with Partial English translation.

Maassen et al., "Strain-dependent induction of cytokine profiles in the gut by orally administered Lactobacillus strains," Vaccine, vol. 18, No. 23, 2000, pp. 2613-2623.

Makras et al., "Kinetic analysis of the antibacterial activity of probiotic lactobacilli towards Salmonella enterica serovar Typhumurium reveals a role for lactic acid and other inhibitory compounds," Research in Microbiology, vol. 157, Apr. 2006, pp. 241-247.

Perdigon et al., "Study of the Possible Mechanisms Involved in the Mucosal Immune System Activation by Lactic Acid Bacteria," Journal of Dairy Science, vol. 82, No. 6, 1999, pp. 1108-1114.

Song et al., "Rapid Identification of 11 human intestinal Lactobacillus species by multiplex PCR assays using group- and species-specific primers derived from the 16S-23S rRNA intergenic spacer region and its flaking 23S rRNA," FEMS Microbiology Lettersm vol. 187, 2000, pp. 167-173.

U.S. Office Action, dated Dec. 23, 2010, for U.S. Appl. No. 11/883,377.

U.S. Office Action, dated Jun. 15, 2011, for U.S. Appl. No. 12/487,978.

U.S. Office Action, dated Nov. 22, 2011, for U.S. Appl. No. 13/208,597.

U.S. Office Action, dated Oct. 12, 2010, for U.S. Appl. No. 12/487,978.

Vietnamese Office Action, dated Jul. 28, 2011, for Vietnamese Application No. 1-2009-01551, including English translation.

Cross et al., "Dietary intake of Lactobacillus rhamnosus HN001 enhances production of both Th1 and Th2 cytokines in antigen-primed mice", Med. Microbiol. Immunol., vol. 191 (2002) pp. 49-53.

Allowed claims in European Patent Application No. 06728662.5.

Pending claims in European Patent Application No. 06728662.5 when the Extended European Search Report issued on Jan. 11, 2012.

Response to Extended European Search Report filed in European Patent Application No. 06728662.5 on Jul. 30, 2012.

European Intention to Grant issued in European Patent Application No. 06 728 662.5 on Nov. 20, 2012.

Extended European Search Report issued in European Patent Application No. 06728662.5 on Jan. 11, 2012.

Marzio et al., "Apoptotic Effects of Selected Strains of Lactic Acid Bacteria on a Human T Leukemia Cell Line are Associated with Bacterial Arginine Deiminase and/or Sphingomyelinase Activities", Nutrition and Cancer, vol. 40, No. 2 (2001) pp. 185-196.

T CELL APOPTOSIS INDUCER AND METHOD THEREFORE

CROSS-REFERENCE TO RELATED APPLICATIONS

This application is a continuation of application Ser. No. 11/883,377, filed on Dec. 4, 2007, now abandoned which is the national stage application of PCT/JP2006/304243 filed on Mar. 6, 2006. This application also claims the benefit of priority of JP 2005-086546 filed on Mar. 24, 2005 and JP 2005-060285 filed on Mar. 4, 2005. The entire contents of all of the above applications are hereby incorporated by reference.

TECHNICAL FIELD

The present invention relates to an inducer of apoptosis of T cells, which comprises a lactic acid bacterial cell as an active component.

BACKGROUND ART

The mammalian immune system protects the host by recognizing bacteria, viruses and kinds of stuff as antigens and eliminating them through the action of the system. The immune system is roughly classified into cellular immunity and humoral immunity, and the both immune systems affect each other to optimize the immune reactions for host defense. T cells participate to play an important role in the modulation of the function of the immune system.

T cells are broadly classified into Th1 and Th2 cells. Th1 cells enhance cellular immunity and Th2 cells enforce humoral immunity. The imbalance in the Th1/Th2 ratio may cause various immune diseases. It is considered that when Th1 cells are dominant, an organ-specific autoimmune disease occurs and when Th2 cells are dominant, a type I allergy or related diseases occur. Therefore, there has been a requirement for a food, a food additive and a medicine, which are useful for realizing the potential for maintaining the Th1/Th2 balance.

References cited herein include Ina K. et al., J. Immunol. 163: 1081, 1999, Boirivant M. et al., Gastroenterology 116: 557, 1999, Watanabe-Fukunaga R. et al., Nature 356:314, 1992, Akdis M. et al., FASEB J. 17: 1026, 2003 and Guerra F. et al., J. Allergy Clin. Immunol. 107:647, 2001.

An object of the present invention is to provide a novel and safe means for inducing apoptosis of excess T cells that may cause various diseases and to facilitate the prevention and cure of a disease such as an organ-specific autoimmune disease or a type I allergy.

DISCLOSURE OF THE INVENTION

The present invention is based on a new finding that when bacterial cells of a specific type of lactic acid bacterial strain is introduced into a state of excess reactivity of T cells, apoptosis of T cells is induced.

The present invention provides an inducer of T cell apoptosis comprising as an active ingredient a lactic acid bacterium belonging to the genus *Lactobacillus* or the genus *Bifidobacterium*. Furthermore, the present invention provides a health food for inducing T cell apoptosis comprising a lactic acid bacterium belonging to the genus *Lactobacillus* or the genus *Bifidobacterium*.

In another aspect, the present invention provides novel lactic acid bacteria, i.e., *Lactobacillus amylovorus* CP1750 (FERM BP-10532), *Bifidobacterium catenulatum* CP2829 (FERM BP-10533) and *Bifidobacterium longum* CP760 (FERM BP-10531).

The inducer of T cell apoptosis according to the present invention is safe even if it is orally taken for a long period of time, because of long experience of usage of lactic acid bacteria as starter cultures for fermentation foods such as yogurt, pickles and the kind of stuff. In addition, it is expected that the inducer of the invention induces apoptosis of excess T cells to prevent and/or cure an inflammatory disease, such as an organ-specific autoimmune disease or an allergy caused by excess T cells.

DETAILED DESCRIPTION OF THE PREFERRED EMBODIMENTS

Figure 1:
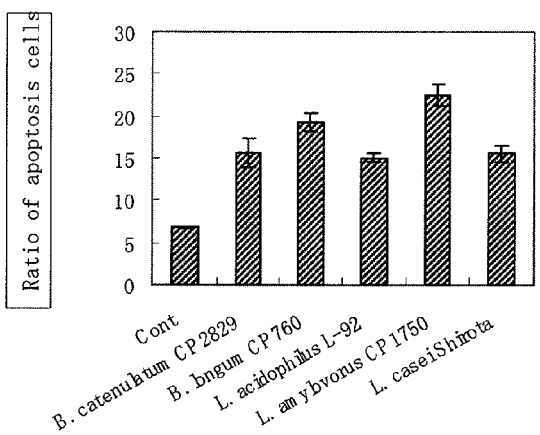
FIG. 1 shows induction of naive T cell apoptosis by a variety of lactic acid bacteria.

The inducer of T cell apoptosis of the present invention comprises a lactic acid bacterium belonging to the genus *Lactobacillus* or the genus *Bifidobacterium* as an active element. As described in Examples below, it was observed in a study where lactic acid bacterial cells are added to T cells derived from spleen cells of mice, showing that such a lactic acid bacterium has an activity of inducing T cell apoptosis.

Examples of the lactic acid bacterium belonging to the genus *Lactobacillus* include *Lactobacillus acidophilus*, *Lactobacillus amylovorus* and kinds of stuff. Examples of the lactic acid bacterium belonging to the genus *Bifidobacterium* include *Bifidobacterium catenulatum*, *Bifidobacterium longum* and et alia.

As the lactic acid bacterium belonging to *Lactobacillus acidophilus* to be used for the inducer of T cell apoptosis of the present invention, a particularly preferred bacterium is *Lactobacillus acidophilus* L-92 (deposited on Mar. 4, 1994 under Accession No. FERM BP-4981 at International Patent Organism Depositary).

*Lactobacillus acidophilus* L-92 has the following microbiological properties.

(Morphological Properties)
1) Morphology: Rods,
2) Motility: Non,
3) Spore: Non,
4) Gram staining: Positive
(Physiological Properties)
1) Catalase: Negative,
2) Formation of indole: Negative,
3) Reduction of nitrate: Negative,
4) Attitude to oxygen: Facultative anaerobic,
5) Growth at 15° C.: Non, 6) Formation of DL lactic acid from glucose by homolactic fermentation, Formation of gas: Non
7) Formation of acid from sugars:

| | | | |
|---|---|---|---|
| Glucose | + | Melibiose | − |
| Lactose | + | Raffinose | + |
| Mannose | + | Mannitol | − |
| Fructose | + | Sorbitol | − |
| Galactose | + | Esculin | + |
| Sucrose | + | Salicin | + |
| Arabinose | − | N-acetylglucosamin | + |
| Maltose | + | Amygdalin | + |
| Xylose | − | Gentiobiose | + |
| Rhamnose | − | Melezitose | − |
| Cellobiose | + | Dextrin | − |
| Trehalose | + | Starch | − |

In addition, as the lactic acid bacterium belonging to *Lactobacillus* to be used for the inducer of T cell apoptosis in the present invention, another particularly preferred bacterium is *Lactobacillus amylovorus* CP1750 (FERM BP-10532). Examples of the lactic acid bacterium belonging to the genus *Bifidobacterium* include *Bifidobacterium catenulatum* CP2829 (FERM BP-10533) and *Bifidobacterium longum* CP760 (FERM BP-10531). These strains were isolated from human intestine and have the following assimilation property.

TABLE 1

| | Strain | *Bifidobacterium catenulatum* CP2829 FERM BP-10533 | *Bifidobacterium longum* CP760 FERM BP-10531 | *Lactobacillus amylovorus* CP1750 FERM BP-10532 |
|---|---|---|---|---|
| | Accession No. | | | |
| 1 | Glycerol | − | − | − |
| 2 | Erythritol | − | − | − |
| 3 | D-arabinose | − | − | − |
| 4 | L-arabinose | + | + | − |
| 5 | Ribose | + | + | − |
| 6 | D-xylose | + | + | − |
| 7 | L-xylose | − | − | − |
| 8 | Adonitol | − | − | − |
| 9 | β-methyl-D-xyloside | − | − | − |
| 10 | Galactose | + | + | + |
| 11 | Glucose | + | + | + |
| 12 | Fructose | + | + | + |
| 13 | Mannose | − | + | + |
| 14 | Sorbose | − | − | − |
| 15 | Rhamnose | − | − | − |
| 16 | Dulcitol | − | − | − |
| 17 | linositol | − | − | − |
| 18 | Mannitol | + | − | − |
| 19 | Sorbitol | + | − | − |
| 20 | α-methyl-D-mannoside | − | − | − |
| 21 | α-methyl-D-glucoside | − | + | − |
| 22 | N-acetylglucosamine | − | − | + |
| 23 | Amygdalin | + | − | − |
| 24 | Arbutin | + | − | − |
| 25 | Esculin | + | − | − |
| 26 | Salicin | + | − | − |
| 27 | Cellobiose | + | + | + |
| 28 | Maltose | + | + | + |
| 29 | Lactose | + | + | + |
| 30 | Melibiose | + | + | − |
| 31 | Saccharose | + | + | + |
| 32 | Trehalose | + | − | − |
| 33 | Inulin | − | − | − |
| 34 | Melezitose | − | + | − |
| 35 | Raffinose | + | + | + |
| 36 | Starch | − | − | + |
| 37 | Glycogen | − | − | − |
| 38 | Xylitol | − | − | − |
| 39 | Gentiobiose | + | − | + |
| 40 | D-turanose | + | + | − |
| 41 | D-lyxose | − | − | − |
| 42 | D-tagatose | − | − | − |
| 43 | D-fucose | − | − | − |
| 44 | L-fucose | − | − | − |
| 45 | D-arabitol | − | − | − |
| 46 | L-arabitol | − | − | − |
| 47 | Gluconate | + | − | − |
| 48 | 2-keto-gluconate | − | − | − |
| 49 | 5-keto-gluconate | − | + | − |

It is known that failure of T cell apoptosis is largely involved in prophylaxis of a disease such as an autoimmune disease or a type I allergy. For example, in a patient with Crohn's disease, which is one of the organ-specific autoimmune diseases, mucosal T cells are resistant to apoptosis (Ina K. et al., J. Immunol. 163: 1081, 1999; Boirivant M. et al., Gastroenterology 116: 557, 1999). In an MRL-lpr/lpr mouse, auto-reactive T cells that should be eliminated by apoptosis under normal conditions are not eliminated and accumulated in the peripheral lymphoid tissues to cause an autoimmune reaction (Watanabe-Fukunaga R. et al., Nature 356:314, 1992). In patients with atopic dermatitis, Th1 cells tend to undergo apoptosis and Th2 cells proliferate (Akdis M. et al., FASEB J. 17: 1026, 2003), while in patients with atopic dermatitis receiving immunotherapy, Th2 cells tend to undergo apoptosis (Guerra F. et al., J. Allergy Clin. Immunol. 107:647, 2001). In other words, it is believed that a disease occurs when excess T cells cannot be eliminated by apoptosis, and the disease can be cured if appropriate apoptosis can be induced.

Accordingly, the inducer of T cell apoptosis of the present invention is considered to be useful for prevention and treatment of a disease such as an allergic disease including atopic dermatitis, Crohn's disease, rheumatic arthritis, multiple sclerosis, systemic lupus erythematosus, scleroderma, Sjogren's syndrome, vitiligo vulgaris, insulin-dependent diabetes mellitus, ankylosing spondylitis and Basedow's disease.

The lactic acid bacterium to be used as the inducer of T cell apoptosis of the present invention may be of any strain of the genus *Lactobacillus* or the genus *Bifidobacterium*. Any medium may be used for the culture of such a lactic acid bacterium, as long as it can support growth of the lactic acid bacterium, including, for example, media containing animal milk, skimmed milk, milk whey, MRS medium, GAM medium, BL medium, Briggs liver broth, a synthetic medium and kinds of stuff. The culture temperature is in the range from 25° C. to 50° C., preferably in the range from 35° C. to 42° C. The culture time is in the range from 3 hours to 48 hours, preferably in the range from 8 hours to 20 hours. Further, neutralization culture or filtration culture may be carried out using any of these media. In addition, as for the fermented lactic acid bacterial cells, the fermented broth may be used as such, or only bacterial cells may be collected by centrifugation or filtration. Further, the bacterial cells can also be used in the form of lyophilized bacterial cells. Further, heat-treated bacterial cells, homogenized bacterial cells and kinds of stuff may also be used. A bacterial cell component is added to any of various food materials, such as drinks, tableted candies, paste, bread and confectionery products to provide a health drink, a health food or a functional food. Further, a medicine containing the bacterial cell component as an active ingredient may be provided.

The inducer of T cell apoptosis of the present invention can be formulated into a pharmaceutical preparation by a method well known to those skilled in the state of art. For example, lactic acid bacterial cells or a processed product thereof can be formulated into a preparation by appropriately combining it with a pharmaceutically acceptable carrier or medium, including sterile water, physiological saline, a plant oil, an emulsifying agent, a suspending agent, a surfactant, a stabilizer, a flavor, an excipient, a vehicle, a preservative, a binder, or the kinds of stuff, and mixing them into a unit dosage form required for generally accepted pharmaceutical practice.

For oral administration, lactic acid bacterial cells or a processed product thereof can be formulated as a tablet, a pill, a sugar-coated agent, a capsule, a liquid, a gel, a syrup, a slurry, a suspension, or the kind of stuff by mixing with a pharmaceutically acceptable carrier well known in the state of art. For parenteral administration, lactic acid bacterial cells or a processed product thereof can be formulated according to standard pharmaceutical practice by using a pharmaceutically acceptable vehicle well known in the state of art.

Examples of an appropriate administration route for the inducer of T cell apoptosis of the present invention include, but not limited to, oral administration, intrarectal administration, transmucosal administration, intestinal administration, intramuscular injection, subcutaneous injection, intramedullary injection, intrathecal injection, direct intraventricular injection, intravenous injection, intravitreous injection, intraperitoneal injection, intranasal injection and intraocular injection. The administration route and method can be appropriately selected depending on the patient's age and their symptoms. Preferably, the inducer of T cell apoptosis of the present invention is orally administered. The administration amount of the inducer of T cell apoptosis of the present invention will depend on the age, body weight, symptoms, therapeutic efficacy, administration method, treatment time or the other conditions, however, it is generally in the range of 1 mg to 1000 mg per dose per adult, and the dose can be orally administered once to several times a day. It should be noted that since the lactic acid bacterium, i.e. the active component is edible, there is no restriction on the administration amount from the view point of safety.

Hereinafter, the present invention is described in more detail with reference to Examples, however, the present invention is not limited to these Examples.

The disclosure of all patents and documents cited herein are entirely incorporated herein as reference. The present application claims priority based on the Japanese Patent Application Nos. 2005-60285 and 2005-86546, the disclosure of which is entirely incorporated herein as reference.

The following examples further illustrate the present invention. The examples below are not limiting and are merely representative of various aspects and features of the present invention.

EXAMPLES

Example 1

Preparation of Lactic Acid Bacteria

Lactic acid bacteria belonging to the genus *Lactobacillus* and lactic acid bacteria belonging to the genus *Bifidobacterium* were cultured at 37° C. for 18 hours in MRS medium and GAM medium, respectively. After the culture, the lactic acid bacterial cells were collected by centrifugation, washed and lyophilized. The dried bacterial cells were suspended in a PBS solution, treated by heating at 100° C. for 10 minutes and used in the following experiments.

Example 2

Induction of Apoptosis of Naive T Cells

Preparation of cells: The spleen was excised from a DO11.10 TCR-transgenic mouse bearing αβ-T cell receptor (TCR) gene derived from a T cell clone DO11.10 that I-A$^d$ restrictively recognizes a region between the 323rd and 339th residues of ovalbumin (hereinafter referred to as OVA), and a single cell suspension was prepared. CD4 microbeads (Miltenyi Biotec) suspended in MACS buffer (PBS containing 0.5% bovine serum albumin and 2 mM EDTA) were reacted with the cell suspension at 4° C. for 15 minutes. After the cells were washed, positive selection was collected using a magnetic separation column (Militenyi Biotec) to prepare CD4-positive T cells. The spleen was excised from a BALB/c mouse and a single cell suspension was prepared. Thy1.2 microbeads (Militenyi Biotec) suspended in MACS buffer were reacted with the cell suspension at 4° C. for 15 minutes. After the cells were washed, the negatively selected cell fraction was collected using a magnetic separation column, and used as antigen-presenting cells.

Culture of cells: The CD4-positive T cells derived from the spleen of a DO11.10 mouse and the antigen presenting cells derived from the spleen of a BALB/c mouse were prepared at $5 \times 10^5$/ml and $1.5 \times 10^6$/ml, respectively, and cultured in RPMI1640 medium (containing 100 units/ml penicillin, 100 µg/ml streptomycin, $5 \times 10^{-5}$ M mercaptoethanol and 0.03% glutamine) containing 5% fetal bovine serum, and then stimulated with 1 mg/ml OVA (Seikagaku Corporation). Heat-killed lactic acid bacterial cells were added (10 µg/ml) and cultured at 37° C. under 5% carbon dioxide gas.

Method of detecting apoptosis: The cells cultured for 4 days were collected and reacted with anti-mouse CD16/32 (FCγIII/II Receptor) antibody (FcBlock™; BD Pharmingen) diluted with FACS buffer (PBS containing 1% fetal bovine serum and 0.1% sodium azide) at 4° C. for 10 minutes to avoid non-specific binding to Fc receptors, and then stained with FITC-labeled KJ1.26 (anti-chronotype antibody against DO11.10 T cell). Then, the cells were stained using Annexin V-PE Apoptosis Detection kit I (BD Pharmingen). The stained cells were detected using FACS LSR (BD) and the percentage of Annexin V-positive cells in KJ1.26-positive cells was determined.

The test results are shown in FIG. 1. An activity of inducing naive T cell apoptosis was observed in all the lactic acid bacteria tested. Further, an assay of cytokine in the culture supernatant showed that IL-2 production was decreased by the antigen stimulation (data not shown).

Example 3

T Cell Apoptosis in Dose-Dependent Manner

The preparation of cells and the detection of apoptosis were carried out in the same manner as in Example 2. The cells were cultured in accordance with Example 2, except that *Lactobacillus acidophilus* L-92 was used at concentrations of 0.1, 1.0 and 10 µg/ml as heat-killed lactic acid bacterial preparations.

Figure 2:
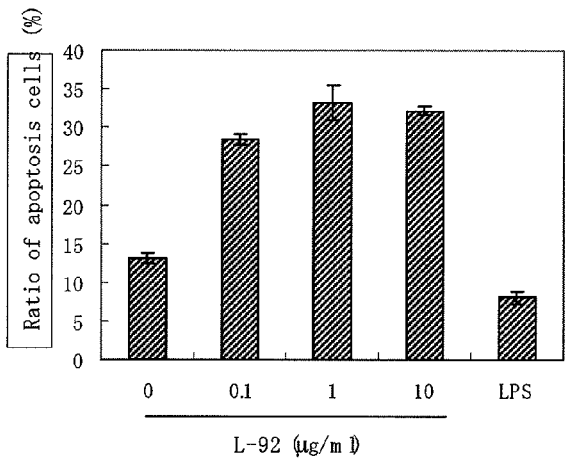
FIG. 2 shows a dose-dependent induction of T cell apoptosis by *Lactobacillus acidophilus* L-92.

The test results are shown in FIG. 2. It was observed that *Lactobacillus acidophilus* L-92 induces T cell apoptosis in a dose-dependent manner.

Example 4

Induction of Th2 Cell Apoptosis

Preparation of Th2 cells: The CD4-positive T cells derived from the spleen of a DO11.10 mouse were prepared at $5 \times 10^5$/ml, and the antigen-presenting cells derived from the spleen of a BALB/c mouse treated with 50 µg/ml mitomycin C (Sigma) at 37° C. for 30 minutes were prepared at $1.5 \times 10^6$/ml. Then, 5 µg/ml anti-mouse IL-4 antibody (clone C17.8) and 2 ng/ml recombinant mouse IL-4 were added to the culture medium and the cells were cultured for 7 days in the presence of 1 mg/ml OVA. Then, the cells were collected and used as Th2 cells. The method of culturing cells and the method of detecting apoptosis are the same as those in Example 2.

Assay of IL-4

Fifty microliters of an anti-IL-4 antibody (clone: 11B11, BD Pharmingen) solution diluted to 1 µg/ml in 0.1 M Na$_2$HPO$_4$ were added to an immunoplate (Nunc), and the plate was left overnight at 4° C., whereby the plate was coated with the antibody. After the wells were washed with PBS containing 0.05% Tween 20 (PBS-Tween), 100 µl of a 1% BSA/PBS-Tween solution was added and the plate was let stand at room temperature for 2 hours to block the plate. After the wells were washed with PBS-Tween, then after, 50 µl of a standard specimen in a serial dilution or each culture supernatant diluted in a 1% BSA/PBS-Tween solution was added to the well, and the plate was kept at room temperature for 2 hours. After the wells were washed with PBS-Tween, 50 µl of a biotinylated anti-IL-4 antibody (clone: BVD4-1D11, BD Pharmingen) diluted to 0.25 µg/ml in a 1% BSA/PBS-Tween solution was added and the plate was stood at room temperature for 2 hours. After the wells were washed with PBS-Tween, 50 µl of an alkaline phosphatase streptavidin (Zymed) solution diluted to 1.5 µg/ml in a 1% BSA/PBS-Tween solution was added and the plate was let stand at room temperature for 1 hour. After the wells were washed with PBS-Tween, 50 µl of 4-nitrophenyl disodium phosphate (Tokyo Kasei Kogyo Co., Ltd.) dissolved in diethanolamine-hydrochloride buffer (pH 8.9) at 1 mg/ml was added and the absorbance at 405 nm was measured.

Figure 3:
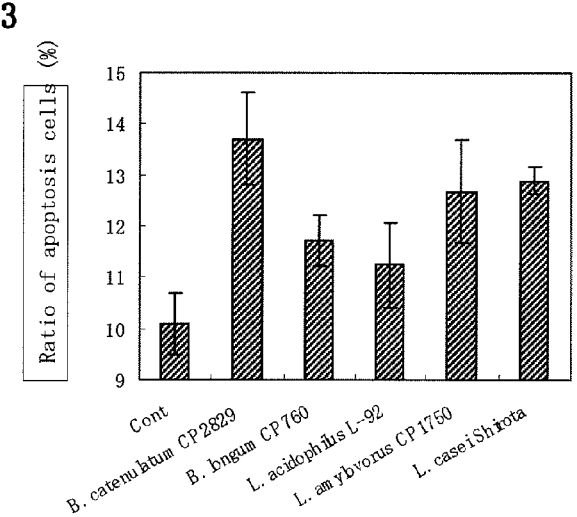
FIG. 3 shows induction of Th2 cell apoptosis by a variety of lactic acid bacteria.
Figure 4:
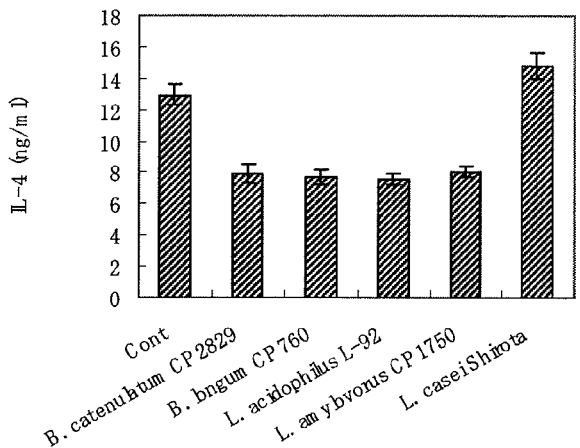
FIG. 4 shows level of IL-4 produced by Th2 cells treated with a variety of lactic acid bacteria.

The test results are shown in FIGS. 3 and 4. An activity of inducing apoptosis of Th2 cells was observed in all the lactic acid bacteria tested (FIG. 3). Furthermore, the level of IL-4 produced by Th2 cells was decreased, demonstrating that Th2 cells were indeed decreased by apoptosis (FIG. 4).

Example 5

Induction of Th1 Cell Apoptosis

Induction of Th1 cells: The CD4-positive T cells derived from the spleen of a DO11.10 mice were prepared at $5 \times 10^5$/ml, and the antigen presenting cells derived from the spleen of BALB/c mice treated with 50 µg/ml mitomycin C (Sigma) at 37° C. for 30 minutes were prepared at $1.5 \times 10^6$/ml. Then, 5 µg/ml anti-mouse IL-4 antibody and 2 ng/ml recombinant mouse IL-12 were added to the culture medium and the cells were cultured for 7 days in the presence of 1 mg/ml OVA. Then, the cells were collected and used as Th1 cells. The method of culturing cells and the method of detecting apoptosis are the same as those in Example 2.

Figure 5:
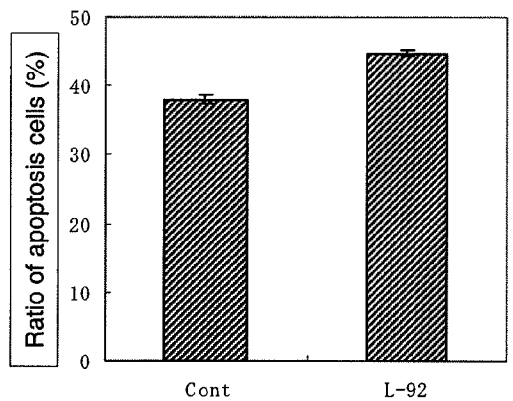
FIG. 5 shows induction of Th1 cell apoptosis by *Lactobacillus acidophilus* L-92.

The test results are shown in FIG. 5. The strain L-92 was demonstrated to have an activity of inducing Th1 cell apoptosis. The results from Examples 2 to 5 suggested that the strain L-92 may suppress overexpression of activated T cells by inducing apoptosis in T cells stimulated by an antigen.

Example 6

Induction of Apoptosis in Spleen and Mesenteric Lymph Nodes

To transgenic mice with OVA-specific T cell receptors (DO11.10 mice), 2% OVA (Wako Pure Chemical Industries Ltd., Cat. No. 012-09885) aqueous solution was given as drinking water. The control group mice received normal CE-2 diet, and the L-92 group mice received CE-2 diet containing 0.05% heat-killed L-92 cells. Also the non-treated group (NT group) mice received normal water and normal CE-2 diet. Seven days later, the spleen and the mesenteric lymph nodes were excised, and the percentage of OVA antigen-specific T cells was determined by double staining with an FITC-labeled anti-CD4 antibody and a PE-labeled KJ1.26 antibody (OVA-TCR-specific antibody) using a flow cytometer.

Figure 6:
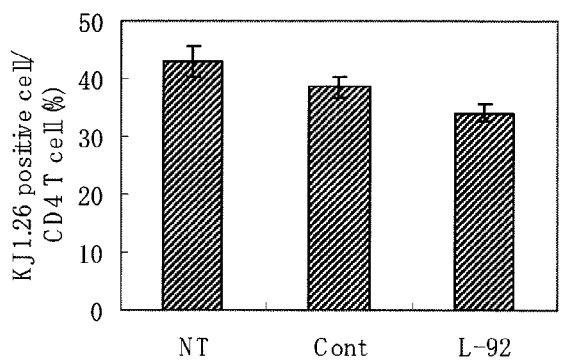
FIG. 6 shows induction of apoptosis of T cells in spleen.
Figure 7:
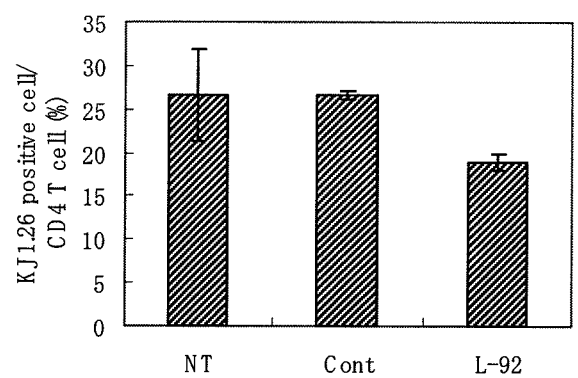
FIG. 7 shows induction of apoptosis of T cells in mesenteric lymph nodes.

The test results are shown in FIG. 6 (spleen) and FIG. 7 (mesenteric lymph nodes). A decrease in antigen-specific T cells was also observed in these tissues of the animals, demonstrating that the strain L-92 has some effect on the immune system and induces apoptosis in antigen-specific T-cells even when orally administrated.

INDUSTRIAL APPLICABILITY

The inducer of T cell apoptosis according to the present invention is safe when orally taken for a long period of time, because it comprises a lactic acid bacterium. Further, it induces apoptosis of excess T cells, therefore it can be expected to prevent and/or cure an inflammatory disease caused by excess T cells, such as an organ-specific autoimmune disease or allergy.

The invention claimed is:

1. A method for inducing T cell apoptosis comprising: administering to a subject in need thereof a biologically pure lactic acid bacterium belonging to the genus *Lactobacillus* or the genus *Bifidobacterium* as an active ingredient and a carrier, wherein the biologically pure lactic acid bacterium is selected from the group consisting of *Lactobacillus acidophilus* strain FERM BP-4981, *Lactobacillus amylovorus* strain FERM BP-10532, *Bifidobacterium catenulatum* strain FERM BP-10533 and *Bifidobacterium longum* strain FERM BP-10531.

2. The method according to claim 1, wherein the active ingredient comprising the biologically pure lactic acid bacterium selected from the group consisting of *Lactobacillus acidophilus* strain FERM BP-4981, *Lactobacillus amylovorus* strain FERM BP-10532, *Bifidobacterium catenulatum* strain FERM BP-10533 and *Bifidobacterium longum* strain FERM BP-10531 is in a health food.

3. The method according to claim 1, wherein the biologically pure lactic acid bacterium is orally administered.

4. The method according to claim 1, wherein Th2 cell apoptosis is induced.

5. The method according to claim 1, wherein Th1 cell apoptosis is induced.

6. The method according to claim 1, wherein both Th1 cell and Th2 cell apoptosis is induced.

7. The method according to claim 1, wherein said method further involves a decrease of Il-4 production.

8. The method according to claim 1, wherein apoptosis in antigen-specific T-cells is induced.

9. The method according to claim 1, wherein apoptosis in spleen and mesenteric lymph nodes is induced.

10. A biologically pure lactic acid bacterium, *Lactobacillus amylovorus* strain FERM BP-10532.

11. A biologically pure lactic acid bacterium, *Bifidobacterium catenulatum* strain FERM BP-10533.

12. A biologically pure lactic acid bacterium, *Bifidobacterium longum* strain FERM BP-10531.

* * * * *